US008063235B2

(12) United States Patent
Krumbholz et al.

(10) Patent No.: US 8,063,235 B2
(45) Date of Patent: Nov. 22, 2011

(54) CROMATOGRAPHY PROCESS FOR RECOVERING A SUBSTANCE OR A GROUP OF SUBSTANCES FROM A MIXTURE

(75) Inventors: Rudolf Krumbholz, Merchweiler (DE); Peter Lembke, Gersheim-Herbitzheim (DE); Norbert Schirra, Voelklingen (DE)

(73) Assignee: K.D. Pharma Bexbach GmbH, Bexbach (DE)

( * ) Notice: Subject to any disclaimer, the term of this patent is extended or adjusted under 35 U.S.C. 154(b) by 349 days.

(21) Appl. No.: 12/305,942

(22) PCT Filed: Jun. 19, 2007

(86) PCT No.: PCT/EP2007/005379
§ 371 (c)(1),
(2), (4) Date: Dec. 19, 2008

(87) PCT Pub. No.: WO2007/147554
PCT Pub. Date: Dec. 27, 2007

(65) Prior Publication Data
US 2011/0015418 A1    Jan. 20, 2011

(30) Foreign Application Priority Data
Jun. 19, 2006  (EP) .................................... 06115656

(51) Int. Cl.
*C11B 7/00* (2006.01)
*C11B 3/10* (2006.01)

(52) U.S. Cl. ........ 554/191; 554/165; 554/175; 554/193; 554/194; 554/196; 554/205

(58) Field of Classification Search ........................ None
See application file for complete search history.

(56) References Cited

FOREIGN PATENT DOCUMENTS
EP              0379963 A1      8/1990

OTHER PUBLICATIONS

Alkio, M. et al. 2000 "Purification of polyunsaturated fatty acid esters from tuna oil with supercritical fluid chromatography" *J American Oil Chemists* 77:315-321.
Higashidate, S. et al. 1990 "Enrichment of eicosapentaenoic acid and docosahexaenoic acid esters from esterified fish oil by programmed extraction-elution with supercritical carbon dioxide" *J Chromatography* 515:295-303.

(Continued)

*Primary Examiner* — Porfirio Nazario Gonzalez
*Assistant Examiner* — Yate K Cutliff
(74) *Attorney, Agent, or Firm* — Knobbe Martens Olson & Bear LLP (57) ABSTRACT

Method for improving the performance of a preparative batchwise Super Critical Fluid Chromatographic separation for the recovery of a target fatty acid or derivative thereof, or of a group of target fatty acids or of derivatives thereof from a mixture, characterized in that the said Super Critical Fluid Chromatographic separation employs a chromatographic column charged with a stationary phase chosen from the group consisting of aluminium oxide or aluminium oxides, titanium oxide or titanium oxides, silica gel or silica gels, amino propyl modified silica gels, diol modified silica gels, phenyl modified silica gels and "reversed phase" phases, the former in turn chosen from the group consisting of RP18, RP8 and RP3, and in that the said Super Critical Fluid Chromatographic Separation further employs a mobile phase chosen from the group consisting of ethylene, propane, ammonia, dinitrogen dioxide and $CO_2$, wherein in the said method, during the run of the said mixture on the chromatographic column, a pressure and/or temperature gradient is applied to the chromatographic column during the elution of the target fatty acid or derivative thereof.

18 Claims, 10 Drawing Sheets

Example 7

OTHER PUBLICATIONS

Klesper, E. et al. 1988 "Gradient methods in supercritical fluid chromatography" *J Supercritical Fluids* 1:45-69.

Mishra, V.K. et al. 1993 "Extraction and purification of ω-3 fatty acids with an emphasis on supercritical fluid extraction—A review" *Food Res Int* 26:217-226.

Saito, S. 1995 "Research activities on supercritical fluid science and technology in Japan—A review" *J Supercritical Fluids* 8:177-204.

Smith, R.M. 1999 "Supercritical fluids in separation science—the dreams, the reality and the future" *J Chromatograpy A* 856:83-115.

Staby, A and Mollerup, J. 1993 "Separation of constituents of fish oil using supercritical fluids: A review of experimental solubility, extraction, and chromatographic data" *Fluid Phase Equilibria* 91:349-386.

Nagahama, K. et al. 1993 "Separation of EPA and DHA from preconcentrated $AgNO_3$ aqueous solution by supercritical $CO_2$, $C_2H_4$ and $C_2H_6$" AIChE 1993 Annual Meeting, Nov. 12, 1993, St. Louis, MO.

Nisson, W.B. et al. 1989 "Supercritical fluid fractionation of fish oil esters using incremental pressure programming and a temperature gradient" *J American Oil Chemists* 66:1596-1600.

Figure 1
Example 1

Figure 2
Example 3

Figure 3
Example 4

Figure 4
Example 5

Figure 5
Example 6

Figure 6
Example 7

Figure 7
Example 8

Figure 8.1
Example 9

Figure 8.2
Example 9

Figure 9
Example 10

US 8,063,235 B2

CROMATOGRAPHY PROCESS FOR RECOVERING A SUBSTANCE OR A GROUP OF SUBSTANCES FROM A MIXTURE

This application is U.S. National Phase of International Application PCT/EP2007/005379, filed Jun. 19, 2007 designating the U.S., and published in English as WO 2004/083154 on Sep. 30, 2004, which claims priority to European Patent Application No. EP 06115656.8 filed Jun. 19, 2006.

FIELD OF THE INVENTION

The present invention relates to the recovery of a substance or a group of substances from a mixture, in particular to the recovery by means of preparative SFC separation methods. In the fields of (i) analytical chemistry and of (ii) the recovery of active principles from natural sources on preparative scale, the acronym "SFC" designates "Super Critical Fluid Chromatography". The SFC technique, which is similar to HPLC and which, like the latter one, can adopt both, the use of packed and of open tubular (i.e. capillary) columns, goes back to as early as 1962, but—due to technical problems—the method fell into disuse for a long time. The characterizing feature of SFC is that a so-called supercritical fluid i.e. a unique phase existing in the p,T-diagram of a substance in the area beyond the so-called critical point ($p_{crit}, T_{crit}$), where liquid cannot be distinguished from gas and where the physical properties are intermediate between those two phases, is employed as chromatographic mobile phase. The most widely used stationary phases in packed columns employed in SFC are instead perfectly conventional HPLC phases such as silica and ODS. Polysiloxane-based stationary phases are predominant in capillary SFC.

As regards the mobile phase, the supercritical phase most often used is CO2, due to its comparatively low critical temperature and pressure, its non-toxicity, its compatibility with most detectors, its availability, its low price and its non-flammability.

In the past few years, interest in this technology has been rejuvenated, and activity in the SFC field, mainly (but not only) as regards its analytical applications, has rapidly increased, due to the SFC's outstanding advantages over HPLC which include:

reduction of organic solvent purchase costs,
reduction of organic solvent disposal costs,
reduction of time needed to remove mobile phase from products,
reduction of damage to products resulting from mobile phase removal,
improvement in laboratory safety.

TECHNICAL BACKGROUND

While undergoing now booming development in the analytical field, the SFC technique on preparative scale is however, for the time being, much less established.

Therefore, many natural products are recovered through the employment of more traditional technologies. Among the recovery of natural products, in particular of those employed for pharmaceutical purposes, a particular field of interest is the separation of fatty acids, preferably unsaturated, in particular polyunsaturated fatty acids, such as eicosapentaenoic acid (EPA) and docosahexaenoic acid (DHA) from marine oils, in particular from fish oils. Aforementioned fatty acids are referred to as "omega-3 fatty acids" (more exactly: C20:5 ω-3 and C22:6 ω-3), and the positive health effect brought about by their consumption has been extensively reported in the last 20-25 years.

Since most naturally occurring marine oils are not particularly concentrated in omega-3 fatty acids and since untreated fish oils of medium omega-3 fatty acid content inherently have an unsavory fish odour and flavour, a number of processes have been developed in the last years for refining the crude oils and for separating the omega-3 fractions, such as to provide highly purified preparations employable for pharmaceutical purposes. This is because the employment of lower concentrated preparations is excised by the Pharmacopeia, such that the same can only be exploited as food supplements, not as pharmaceuticals.

Various purification techniques, including urea complexing, adsorption, HPLC, Super critical fluid extraction, fractional and/or molecular distillation etc., have therefore been applied alone or in combination, to purify the omega-3 fractions from marine oils. An example of such previous techniques is given in William B. Nilsson et al. "Supercritical Fluid Fractionation of Fish Oil Esters using Incremental Pressure Programming and a Temperature Gradient." JAOCS, Vol. 66, no. 11 (November 1989). Supercritical fluid fractionation as relied upon by Nilsson et al. is a distillation technique involving the use of a vertical column having an internal structure or packing made of an inert material providing for an increased surface, such as to ease the achievement of an equilibrium between the fluid phases involved. The inert packing material (e.g. Sulzer® packings, Raschig® rings, ball bearings etc.) has an exclusively geometrical function and does not take part, as such, in the phase equilibrium.

However, most of these conventional techniques are cumbersome and time consuming, especially, if they are employed to arrive at highly purified (75% or more) EPA and/or DHA preparations. The use of these methods is therefore mainly indicated for the attainment of pre-purified (or pre-refined) mixtures of fatty acids or of their derivatives, most advantageously of their ethyl esters, to be subjected then to a more efficient final downstream step of improved selectivity.

Therefore, the substrates nowadays employed in the said last refining steps for the manufacture of omega-3 fatty acid based pharmaceuticals are normally pre-enriched ethyl ester compositions derived from marine materials being lower that 75% in EPA and/or DHA.

Among the most recent technological attempts to achieve the final purification with modern separation methods employing supercritical fluids is U.S. Pat. No. 5,719,302 to Perrut et al. who describes, in an attempt to overcome the low productivity achieved heretofore with large scale stationary bed HPLC employed earlier in the art, a process for chromatographic fractionation of fatty acids and their derivatives, such process comprising, in one of its steps, subjection of a feed composition to simulated continuous countercurrent moving bed chromatography with supercritical CO2 as eluent, with the aim of recovering fractions of purified polyunsaturated fatty acids.

However, costs for the construction of a plant of the type used by U.S. Pat. No. 5,719,302 are high, and reduction to practice of the method described therein, in particular the fine tuning of the process parameters, is difficult, such that, to Applicant's knowledge, no preparations obtained with this method have, so far, actually hit the market.

On top of the aforementioned method, some years ago, a mixed preparative SFC/SFE technique "on column" for recovering a substance or a group of substances from a mixture has been proposed, for the first time, by the Applicant of the present invention in order to increase the throughput of batchwise SFC separation, see EP 712 651. SFC/SFE is particularly suited for the separation of fatty acid mixtures and of mixtures of their ethylesters, be the same pre-refined (i.e. pre-enriched) as indicated above, or not. The batchwise mixed preparative SFC/SFE technique can be easily adopted by overloading the employed SFC column in a controlled manner and is operated with success by the Applicant who has a long-grown experience in the field.

However, due to the strongly increasing demand for highly purified products, a continued need of improved, highly preferment separation methods, and as well as of the products thereby obtained, still exists.

It hence appears that there is a problem in the art, calling for the provision of a still improved process, for recovering a substance or a group of substances from a mixture with improved efficiency. The improved process should be able to provide equally pure products as the ones known in less time or in greater amounts, preferably with the possibility to provide, contemporaneously, still more purified products.

SUMMARY OF THE INVENTION

With the aim of solving the above-mentioned problem, the present invention provides a method for improving the performance of a preparative batchwise Super Critical Fluid Chromatographic separation for the recovery of a target fatty acid or derivative thereof, or of a group of target fatty acids or of derivatives thereof from a mixture characterized in that the said Super Critical Fluid Chromatographic separation employs a chromatographic column charged, with a stationary phase chosen from the group consisting of aluminium oxide or aluminium oxides, titanium oxide or titanium oxides, silica gel or silica gels, amino propyl modified silica gels, diol modified silica gels, phenyl modified silica gels and "reversed phase" phases, the former in turn chosen from the group consisting of octadecyl carbon chain ($C_{18}$)-bonded silica (RP18), octyl carbon chain ($C_8$)-bonded silica (RP8) and propyl ($C_3$)-bonded silica (RP3), and in that the said Super Critical Fluid Chromatographic Separation further employs a mobile phase chosen from the group consisting of ethylene, propane, ammonia, dinitrogen dioxide and $CO_2$, wherein in the said method, during the run of the said mixture on the chromatographic column, a pressure and/or temperature gradient is applied to the chromatographic column during the elution of the target fatty acid or derivative thereof.

DESCRIPTION OF THE ATTACHED FIGURES

FIG. 8.1 is is a graphic representation of the content ([weight %], y-axis) of EPA, DHA and SDA recorded after a specified elution time ([min], x-axis) at the output of a chromatographic column charged with an aminopropyl phase operated with SFC/SFE using $CO_2$ at 103 bar and 46° C., the temperature having been lowered, after 40 minutes elution time, within one minute, by 26° C. to 20° C.

FIG. 8.2 is a graphic representation of the amount ([g], y-axis) of EPA, DHA and SDA obtained after a specified elution time ([min], x-axis) at the output of a chromatographic column charged with an aminopropyl phase operated with SFC/SFE using $CO_2$ at 103 bar and 46° C., the temperature having been lowered, after 40 minutes elution time, within one minute, by 26° C. to 20° C.

DETAILED DESCRIPTION OF THE INVENTION

The present invention as herein described, solves the above-mentioned problem by providing a method for improving the throughput of a preparative batchwise SFC separation for the recovery of a target substance or a group of target substances from a mixture speeding up the recovery or increasing the yield of a target substance or substances, yet without reducing the selectivity of the ongoing separation. Preferably, selectivity is even improved. Preferably, the present invention is employed for improving the throughput of preparative batchwise SFC/SFE separations on a chromatographic column. The present invention is particularly suited and preferably employed for the batchwise preparative SFC, preferably SFC/SFE separation of fatty acids, in particular in the recovery of polyunsaturated fatty acids or of their derivates particularly of their esters, more in particular of their ethyl or methyl esters stemming from natural fish oils.

Among the former, EPA and DHA (or their methyl or ethyl esters) and/or their mixtures are particularly preferred.

SFC (or SCF/SFE) columns in the method of the invention contain stationary phases chosen from the group consisting of of aluminium oxide or aluminium oxides, titanium oxide or titanium oxides, silica gel or silica gels, modified silica gels and "reversed phase" phases. In the aforementioned group, the term "modified silica gels" designates in turn stationary phases chosen from the group consisting of amino propyl modified silica gels, diol modified silica gels and phenyl modified silica gels. Always in the aforementioned group, the term "reversed phase" phases designates in turn stationary phases chosen from the group consisting of RP18, RP8 and RP3. The supercritical eluents employed in the method of the present invention are chosen from the group consisting of ethylene, propane, ammonia, dinitrogen dioxide, and carbon dioxide. It is an important feature of the present invention that the stationary phases and the mobile phases employed by the present invention allow for the recovery of the target fatty acid or derivative thereof without the employment of a solvent or further co-solvent which would be liquid at room pressure and room temperature. Employment of solvents or co-solvents of the aforementioned type is undesirable in that the target fatty acid or derivative would then be obtained in a respective solution requiring then a further separation step like, e.g. a distillation for obtaining the desired undiluted target fatty acid or derivative. Among the mobile phases employed by the present invention, the most preferred supercritical eluent is CO2 ($T_{crit}=31.3°$ C., $p_{crit}=73.7$ bar).

As mentioned above, Applicant has employed batchwise preparative SFC methodologies, as well as combined preparative SFC/SFE methodologies for many years for the separation of omega-3 acid ethyl esters, in particular for the "cutting" of highly purified EPA- and DHA-ethylester fractions. However, experience shows that for reaching the necessary selectivity required to obtain fractions of e.g. 80% of purity (or higher) of the target EPA- or DHA-ethylester, the pressures needed to operate the preparative SFC (or SFC/SFE) column were comparatively low, leading in turn to extended elution times from the the column.

In the preparative SFC or SFC/SFE technique, reduction of the elution time from the column can be achieved through an increase of the density of the supercritical CO2 eluent. Such density increase can be brought about by a pressure increase or a temperature decrease.

However, increasing the pressure or decreasing temperature brings about, at the same time, a decrease in selectivity, meaning that the fractions obtained display, then, a reduced purity. In other words, if a target selectivity is to be achieved, pressure and/or temperature are not tunable.

Thus, should one desire to reduce the operation time needed for the separation of a batch of substrate applied to an SFC column, e.g. by increasing pressure or decreasing temperature, one would envisage to increase the elution power through one or both of the aforementioned measures, exclusively when the target component has been cleared from the column. Such an approach is deemed particularly critical in industrial practice, where the fractions obtained from the individual runs of separate batches are intended for pooling, i.e. meaning that a selectivity drop occurring even intermediately during one single run would render unacceptable the whole yield of several of repeated operations.

The former is reflected by the fact that while literature reports on the adoption of pressure and temperature gradients in SFC methods, the said adoption of pressure and temperature gradients is strictly confined, on the one hand, to analytical, in particular to analytical capillary SFC. It is a characterizing feature of analytical systems that they are abundantly selective (the long capillary columns normally employed for analytical purposes providing for several thousands of theoretical plates) and thus the expected reduction of selectivity brought about by the application of a gradient is—always in analytical systems—not of particular concern, compared to the more urgent necessity of clearing the fractions from the column in reasonable time.

On the other hand, the employment of temperature and pressure stages can be found in preparative SFC (where the maintenance of optimum selectivity is, instead, imperative since the number of available theoretical plates is kept purposively as low as possible), but there exclusively in association with SMB ("simulated moving bed") technology, i.e. with the continuously operated SFC. It is yet an important and critical feature of SMB, that, if so, the specific pressures and temperatures employed within the single stages remain, at any rate, strictly constant throughout the whole separation, i.e. any modulation of pressure and/or temperature within an individual stage is carefully avoided. This is because one has to fear otherwise that changes of pressure and/or temperature within a single stage may lead, during the separation, to the generation of non-reproducible or not properly separated fractions, spoiling the material recovered.

Before this background, achievement of the object of the present invention, namely to reduce the elution time and/or to increase the yield of the target products in batchwise operated SFC (or SFC/SFE) methods, yet without decreasing, at the same time, the target selectivity of the separation of the single components was highly desirable. Even more desirable appeared to be the additional possibility of achieving possibly even a contemporaneous increase of the target selectivity.

Applicant has now surprisingly found that the above-mentioned object, i.e. the improvement of the separation performance, can be achieved in batchwise operated preparative SFC separation methods and in batchwise operated SFC/SFE separation methods, through the application of a pressure- or temperature gradient to the system during elution of the target substance. Namely, it has been unexpectedly discovered that when e.g. a pressure gradient is applied to a batchwise operated preparative SFC separation method, the resulting overall selectivity—instead of lying between the characteristic selectivities associated, respectively with the initial and the final pressure—, is retained at least the level associated with the initial pressure. It has also been found that the same surprizing effect may be obtained applying a temperature gradient or by applying a combination of temperature and pressure gradient. The aforementioned gradients, alone or in their combination, can be applied in continuous or stepwise manner. Preferably, the gradients may be applied before 85% of the target substance is eluted, more preferably before 50% of the target substance is eluted, and still more preferably before 40% of the target substance is eluted.

As regards the pressure and temperature differences actually introduced by the above gradients into the batchwise operated SFC (or SFC/SFE) separation methods of the present invention, it has also been surprisingly found that particularly favourable results are obtained if the target values of temperature and/or pressure lie below the respective critical values of the medium employed.

It is thus preferable if at least one of the target values set for the above-mentioned gradient lies outside of the supercritical area (in the p,T-diagram) of the medium employed.

In particular, Applicant has found, that it is particularly advantageous, if the temperature gradient applied during elution of the target substance is such that the target temperature is smaller than the critical temperature. Namely, it has been found that the former variant is preferable over a specular approach with the target pressure being lower than the critical pressure and the temperature overcritical.

This means that the introduction of a gradient during elution of the target substance, as proposed by the present invention, allows, in preferred embodiments, even for the running of a mixed modus, namely starting as SFC (or SFC/SFE) and switching during operation (be it in a continuously or stepwise manner)—always during elution of the target substance—to an SbFC (or SbFC/SbFE) or even LFC (or LFC/LFE) modus depending on whether just one of p or T (preferably T), or both of them are driven out of their critical range.

Surprisingly, applying such mixed modus, the performance of the batchwise separation still increases, as compared to the driving of a p- and/or T-gradient not leaving the critical area, even in cases where the separation performance as such (i.e. without applying any gradient) outside the critical area is known to be at most comparable or lower than inside the critical area.

Applicant's invention will be more apparent from (yet not limited by) the Examples recited hereinafter.

EXAMPLES

In the following, all purity values are reported as % by weight.

In all the following examples for the purification of each batch, 1.2 kg of starting product were applied to a preparative separation column (inox) of 50 liters (1850×240 mm) packed with the materials specified below. The flowrate was in all the following examples 300 kg $CO_2$ per hour.

The starting product employed in all of the following examples was a mixture of omega 3-enriched fatty acid ethyl esters.

Such starting products are available on the market and are normally obtained trough a pre-purification sequence beginning with trans-esterification of omega 3-rich fish oils. Thereafter, the omega-3 content of the so-obtained ethyl esters is increased by urea precipitation, and the so-obtained ethyl ester mixture is then further pre-refined by means of SFE. The head fraction of the SFE treatment is then employed as the starting product in the following examples.

Examples 1-5

The following examples 1-5 were run on the column as above, filled with a packing of modified silica gel, amino propyl phase, particle size 20-40 micrometers.

Example 1

Comparative

The starting product was applied to the preparative column operated with the supercritical $CO_2$ as eluent and 5 fractions of the eluate (labelled as batch no. 1489/1) were collected and analysed.

Figure 1:
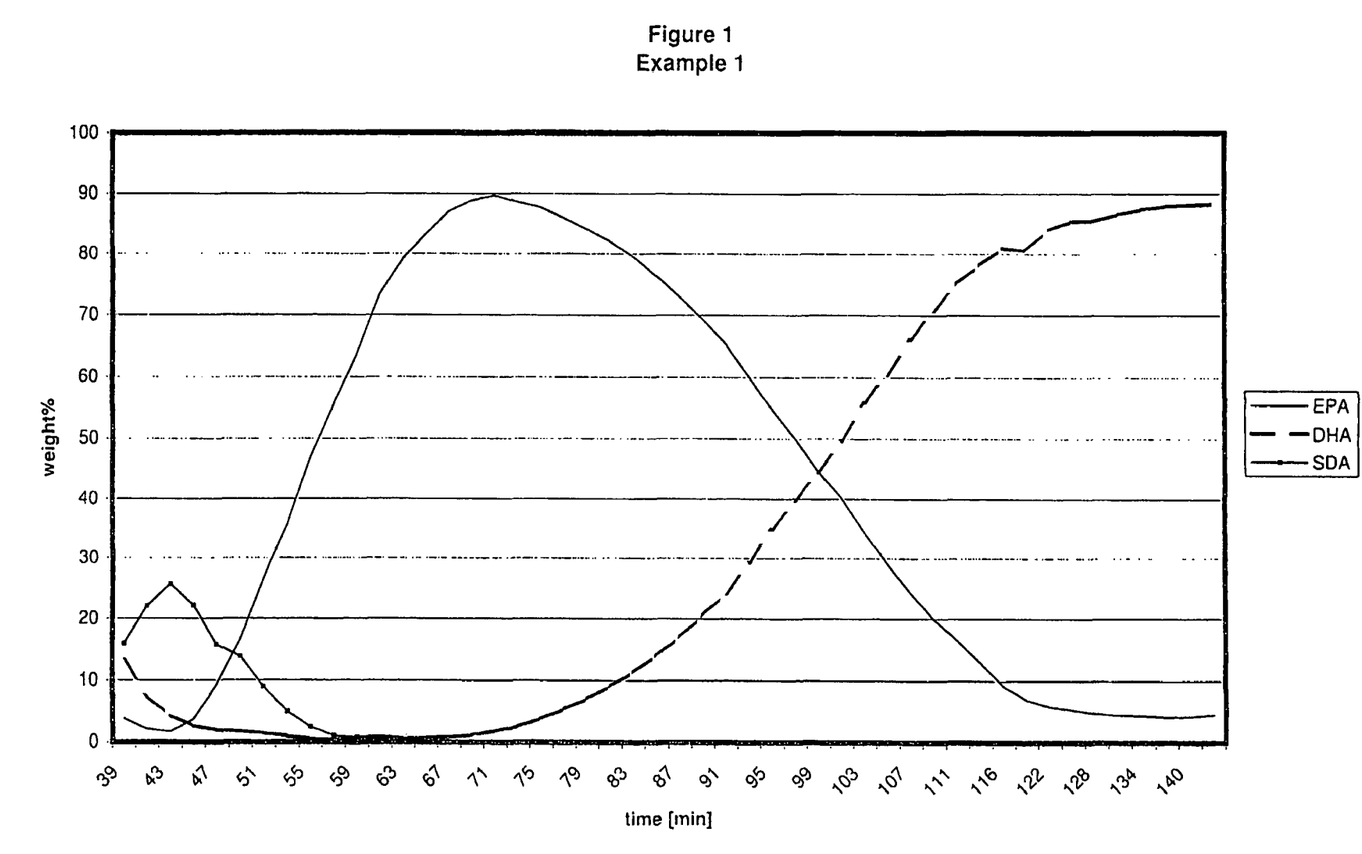
FIG. 1 is a graphic representation of the content ([weight %], y-axis) of EPA, DHA and SDA recorded after a specified elution time ([min], x-axis) at the output of a chromatographic column charged with an aminopropyl phase, operated with SFC/SFE using $CO_2$ at 97 bar and 46° C.

The results can be seen in FIG. 1 which shows that on the said preparative cromatographic column, run with SFC/SFE methods for separating DHA and EPA from each other and, at the same time, from stearidonic acid, in order to obtain respective fractions with (rounded off) purity of at least 85% of EPA and of at least 80% of DHA, (that is to say of at least 80% of each, EPA and DHA), 137 min elution time are needed to recover both fractions, if one operates at a pressure of 97 bar and at a temperature of 46° C.

The results are shown in table 1, displaying the 5 fractions which were cut and analyzed.

TABLE 1

| Batch no. 1489 (run at T = 46° C. and p = 97 bar) | | | | |
|---|---|---|---|---|
| Name of fraction | m [g] | EPA (%) | DHA (%) | SDA (%) |
| SDA | 90.4 | 17.9 | 2.2 | 14.0 |
| SDA/EPA | 157.2 | 61.4 | 0.6 | 0.9 |
| EPA | 575.4 | 85.5 | 3.3 | 0.0 |
| EPA/DHA | 247.6 | 57.9 | 31.9 | 0.0 |
| DHA | 122.0 | 10.6 | 79.9 | 0.0 |
|  | 1192.6 |  |  |  |
| Total Elution time: 137.0 Minutes | | | | |
| Per time unit*: |  | EPA (%) | DHA (%) | SDA (%) |
| SDA | 90.4 | 17.9 | 2.2 | 14.0 |
| SDA/EPA | 157.2 | 61.4 | 0.6 | 0.9 |
| EPA | 575.4 | 85.5 | 3.3 | 0.0 |
| EPA/DHA | 247.6 | 57.9 | 31.9 | 0.0 |
| DHA | 122.0 | 10.6 | 79.9 | 0.0 |
|  | 1192.6 |  |  |  |

*In the lower part of table 1, each fraction is reported with respect to the relative elution time (137 min/137 min = 1), which has been set as "1" for comparative purposes with the following examples 2-5.

Example 2

Comparative

The starting product was applied to the same preparative column, and 5 fractions of the thereby obtained eluate (batch no. 1485) were cut as in example 1. As can be seen from table 2, if the separation is carried out at 46° C. and at 110 bar, the elution time is reduced to 65 minutes, but the obtainable (rounded off) purity of the target fraction EPA does not go beyond 75%, whereas the purity of the DHA fraction is even reduced to 63%. This shows that increasing pressure, a reduced elution time (higher throughput) can be obtained, but to the detriment of selectivity.

TABLE 2

| Batch no. 1485 (run at 46° C. and at 110 bar) | | | | |
|---|---|---|---|---|
| Name of fraction | m [g] | EPA (%) | DHA (%) | SDA (%) |
| SDA | 100.0 | 40.0 | 2.8 | 12.7 |
| SDA/EPA | 226.0 | 66.0 | 7.2 | 11.0 |
| EPA | 580.8 | 75.0 | 12.0 | 3.0 |
| EPA/DHA | 174.2 | 56.8 | 32.6 | 0.6 |
| DHA | 110.0 | 19.1 | 62.5 | 0.6 |
|  | 1191.0 |  |  |  |
| Total elution time: 65.0 Minutes | | | | |
| Recovery per time unit* |  | EPA (%) | DHA (%) | SDA (%) |
| SDA | 210.8 | 40.0 | 2.8 | 12.7 |
| SDA/EPA | 476.3 | 66.0 | 7.2 | 11.0 |
| EPA | 1224.1 | 75.0 | 12.0 | 3.0 |
| EPA/DHA | 367.2 | 56.8 | 32.6 | 0.6 |
| DHA | 231.8 | 19.1 | 62.5 | 0.6 |
|  | 2510.3 |  |  |  |

*reported with respect to the "relative elution time", i.e. 137 min/65 min = 2.11.

Example 3

Invention

Figure 2:
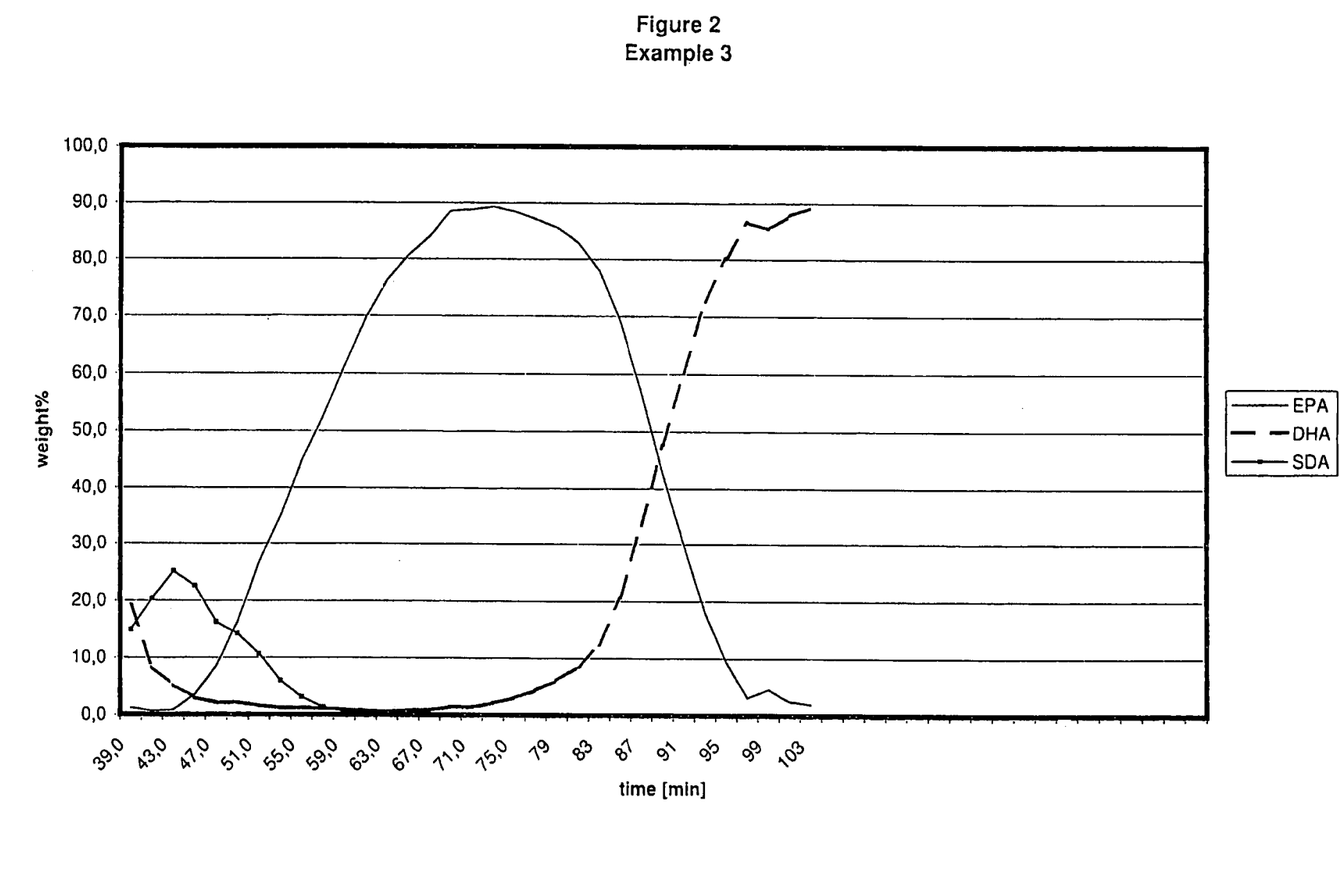
FIG. 2 is a graphic representation of the content ([weight %], y-axis) of EPA, DHA and SDA recorded after a specified elution time ([min], x-axis) at the output of a chromatographic column charged with an aminopropyl phase operated with SFC/SFE using $CO_2$ at 97 bar and 46° C., the pressure having been raised, after 80 minutes elution time, within one minute, by 50 bar to 147 bar.

The starting product was applied to the same preparative column, and 5 fractions of the thereby obtained eluate (batch no. 1488) were cut as in example 1. As can be seen from FIG. 2 and from table 3, if the separation is carried out at 46° C. and at 97 bar for 80 minutes, whereafter, always maintaining the temperature at 46° C., the pressure is increased (within one minute, that is to say still during elution of the EPA fraction) to 97+50=147 bar, the total elution time is reduced to 103 minutes, whereas the obtainable (rounded off) purity of the target fractions EPA and DHA becomes again at least 80%.

TABLE 3

Batch no. 1488
(run at 46° C. for 80' at 97 bar, whereafter the pressure
is increased by within 1' by 50 bar)

| Name of fraction | m [g] | EPA (%) | DHA (%) | SDA (%) |
|---|---|---|---|---|
| SDA | 64.0 | 13.2 | 2.8 | 16.2 |
| SDA/EPA | 242.0 | 66.6 | 0.9 | 0.7 |
| EPA | 502.0 | 85.5 | 4.6 | 0.0 |
| EPA/DHA | 255.0 | 51.9 | 38.2 | 0.0 |
| DHA | 109.0 | 10.0 | 80.2 | 0.0 |
| | 1172.0 | | | |

Total elution time: 99.0 Minutes

| Recovery per time unit*: | EPA (%) | DHA (%) | SDA (%) |
|---|---|---|---|
| SDA | 88.6 | 13.2 | 2.8 | 16.2 |
| SDA/EPA | 334.9 | 66.6 | 0.9 | 0.7 |
| EPA | 694.7 | 85.5 | 4.6 | 0.0 |
| EPA/DHA | 352.9 | 51.9 | 38.2 | 0.0 |
| DHA | 150.8 | 10.0 | 80.2 | 0.0 |
| | 1621.9 | | | |

*reported with respect to the "relative elution time", i.e. 137 min/99 min = 1.38.

Example 4

Invention

Figure 3:
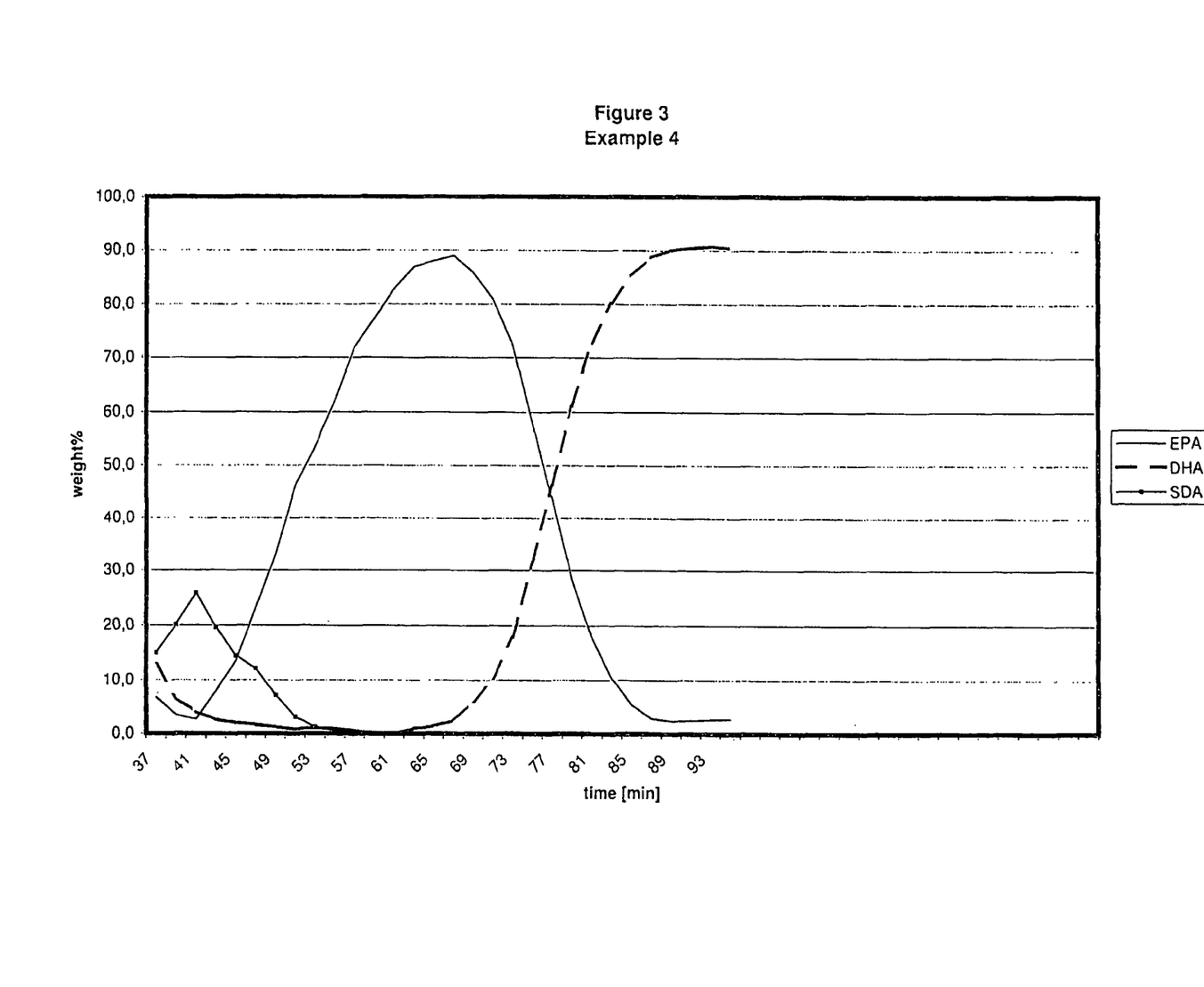
FIG. 3 is a graphic representation of the content ([weight %], y-axis) of EPA, DHA and SDA recorded after a specified elution time ([min], x-axis) at the output of a chromatographic column charged with an aminopropyl phase operated with SFC/SFE using $CO_2$ at 97 bar and 46° C., the pressure having been raised, after 65 minutes elution time, within one minute, by 50 bar to 147 bar.

The starting product was applied to the same preparative column, and 5 fractions of the thereby obtained eluate (batch no. 1493) were cut as in example 1. As can be seen from FIG. 3 and from table 4, if the separation is carried out at 46° C. and at 97 bar for 65 minutes, whereafter, always maintaining the temperature at 46° C., the pressure is increased (within one minute, that is to say still during elution of the EPA fraction) to 97+50=147 bar, the total elution time is reduced to 91 minutes, whereas the obtainable (rounded off) purity of the target fractions EPA and DHA becomes again at least 80% (in particular at least 85% for EPA and at least 80% for DHA).

TABLE 4

Batch no.: 1493
(run at 46° C.
for 65' at 97 bar, whereafter the pressure
is increased by within 1' by 50 bar)

| Name of fraction | M [g] | EPA (%) | DHA (%) | SDA (%) |
|---|---|---|---|---|
| SDA | 83.1 | 18.3 | 2.3 | 14.2 |
| SDA/EPA | 159.0 | 60.2 | 0.8 | 1.0 |
| EPA | 440.6 | 85.4 | 2.5 | 0.0 |
| EPA/DHA | 358.7 | 61.0 | 29.2 | 0.0 |
| DHA | 128.8 | 9.2 | 81.8 | 0.0 |
| | 1170.2 | | | |

Total elution time: 91.0 Minutes

| Recovery per time unit*: | EPA(%) | DHA(%) | SDA(%) |
|---|---|---|---|
| SDA | 125.1 | 18.3 | 2.3 | 14.2 |
| SDA/EPA | 239.4 | 60.2 | 0.8 | 1.0 |
| EPA | 663.3 | 85.4 | 2.5 | 0.0 |
| EPA/DHA | 540.0 | 61.0 | 29.2 | 0.0 |
| DHA | 193.9 | 9.2 | 81.8 | 0.0 |
| | 1761.7 | | | |

*reported with respect to the "relative elution time", i.e. 137 min/91 min = 1.51.

Example 5

Invention

Figure 4:
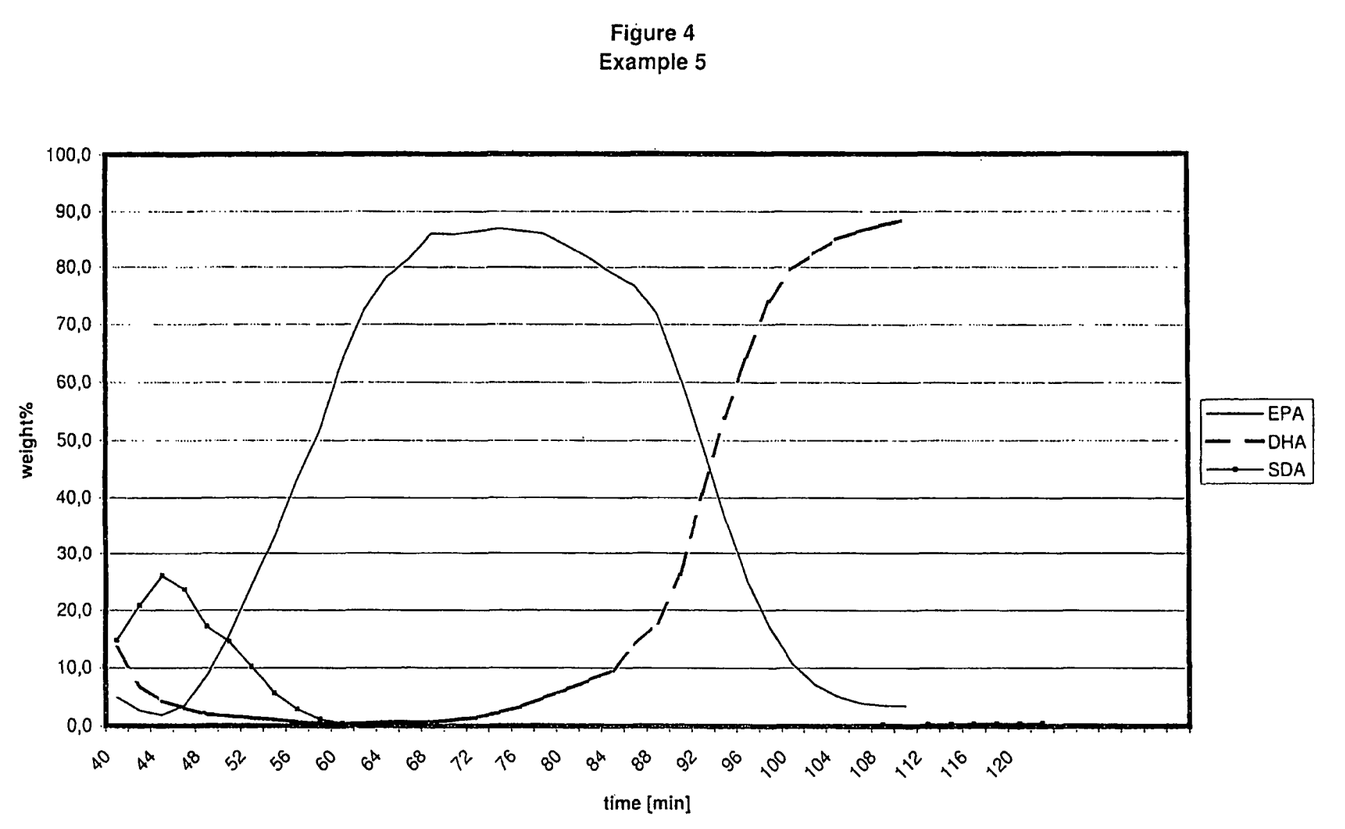
FIG. 4 is a graphic representation of the content ([weight %], y-axis) of EPA, DHA and SDA recorded after a specified elution time ([min], x-axis) at the output of a chromatographic column charged with an amino propyl phase operated with SFC/SFE using $CO_2$ at 97 bar and 46° C., the temperature having been lowered, after 80 minutes elution time, within one minute, by 6° C. to 40° C.

The starting product was applied to the same preparative column, and 5 fractions of the thereby obtained eluate (batch no. 1490) were cut as in example 1. As can be seen from FIG. 4 and from table 5, if the separation is carried out at 46° C. and at 97 bar for 80 minutes, whereafter, always maintaining the pressure at 97 bar, the temperature is reduced (within one minute, that is to say still during elution of the EPA fraction) to 40° C., the total elution time is reduced to 112 minutes, whereas the obtainable (rounded off) purity of the target fractions EPA and DHA becomes again at least 80%, in particular it increases even to at least 84%. (in particular at least 85% for EPA and at least 84% for DHA).

TABLE 5

Batch no.: 1490
(run at 46° C. for 80' at 97 bar, whereafter the temperature is
decreased by within 1' by 6° C.)

| Name of fraction | M [g] | EPA (%) | DHA (%) | SDA (%) |
|---|---|---|---|---|
| SDA | 70.8 | 12.6 | 2.5 | 16.7 |
| SDA/EPA | 227.1 | 61.3 | 0.6 | 1.2 |
| EPA | 482.7 | 85.2 | 2.7 | 0.0 |
| EPA/DHA | 348.4 | 53.2 | 36.2 | 0.0 |
| DHA | 106.1 | 6.2 | 84.4 | 0.1 |
| | 1235.1 | | | |

Total elution time: 112.0 Minutes

| Recovery per time unit*:: | EPA(%) | DHA(%) | SDA(%) |
|---|---|---|---|
| SDA | 113.3 | 12.6 | 2.5 | 16.7 |
| SDA/EPA | 363.6 | 61.3 | 0.6 | 1.2 |
| EPA | 588.9 | 85.2 | 2.7 | 0.0 |
| EPA/DHA | 557.8 | 53.2 | 36.2 | 0.0 |
| DHA | 169.9 | 6.2 | 84.4 | 0.1 |
| | 1977.3 | | | | reported with respect to the "relative elution time", i.e. 137 min/112 min = 1.22.

From the above examples 1-5 it thus appears, that compared to an isothermic/isobaric approach (comparative examples 1 and 2), with the adoption of a pressure or a temperature gradient applied during recovery of the EPA fraction, a yield per time increase is obtainable, whithout selectivity loss.

Examples 6-10

The following examples 1-5 were run on the column as above, filled with a packing of modified silica gel, aminopropyl phase, particle size 20-40 micrometers.

Example 6

Comparative

The starting product was applied to the preparative column as above, operated at 120 bar and 46° C. The results can be seen in FIG. 5 which shows that on the said preparative cromatographic column, run with SFC/SFE methods for separating DHA and EPA from each other and, at the same time, from stearidonic acid, in order to obtain respective fractions with a (rounded off) peak purity of 84% of EPA, 60 min elution time are needed to recover both fractions. The yield of the EPA>80% fraction was 26%. See FIG. 5.

Example 7

Invention

The starting product was applied to the preparative column as above, operated at 103 bar and 46° C. for 40 minutes, whereafter the pressure was increased within one minute by 50 bar to 153 bar [for a constant run at 103 bar, see comparative example 10 below]. The results can be seen in FIG. 6 which shows that on the said preparative cromatographic column, run with SFC/SFE methods for separating DHA and EPA from each other and, at the same time, from stearidonic acid, it was possible to obtain an EPA fraction with a (rounded off) peak purity higher than 90% of EPA in 67 min elution time needed to recover both fractions. The yield of the EPA>90% fraction was 14%, whereas the yield of the EPA>80% fraction was 52%), showing the increased performance of the herein described method. See FIG. 6.

Example 8

Invention

The starting product was applied to the preparative column as above, operated at 103 bar and 46° C. for 40 minutes, whereafter the temperature was decreased within one minute by 6° C. to 40° C. The results can be seen in FIG. 7 which shows that on the said preparative cromatographic column, run with SFC/SFE methods for separating DHA and EPA from each other and, at the same time, from stearidonic acid, it was possible to obtain an EPA fraction with a (rounded off) peak purity of 85% of EPA in 67 min elution time needed to recover both fractions. While this was not a major increase in peak purity as compared to example 6, it must be noted that the yield of the EPA>80% fraction was increased from 26% (example 6) to 47% (here), showing the increased performance of the herein described method. See FIG. 7.

Example 9

Invention

Figure 81:
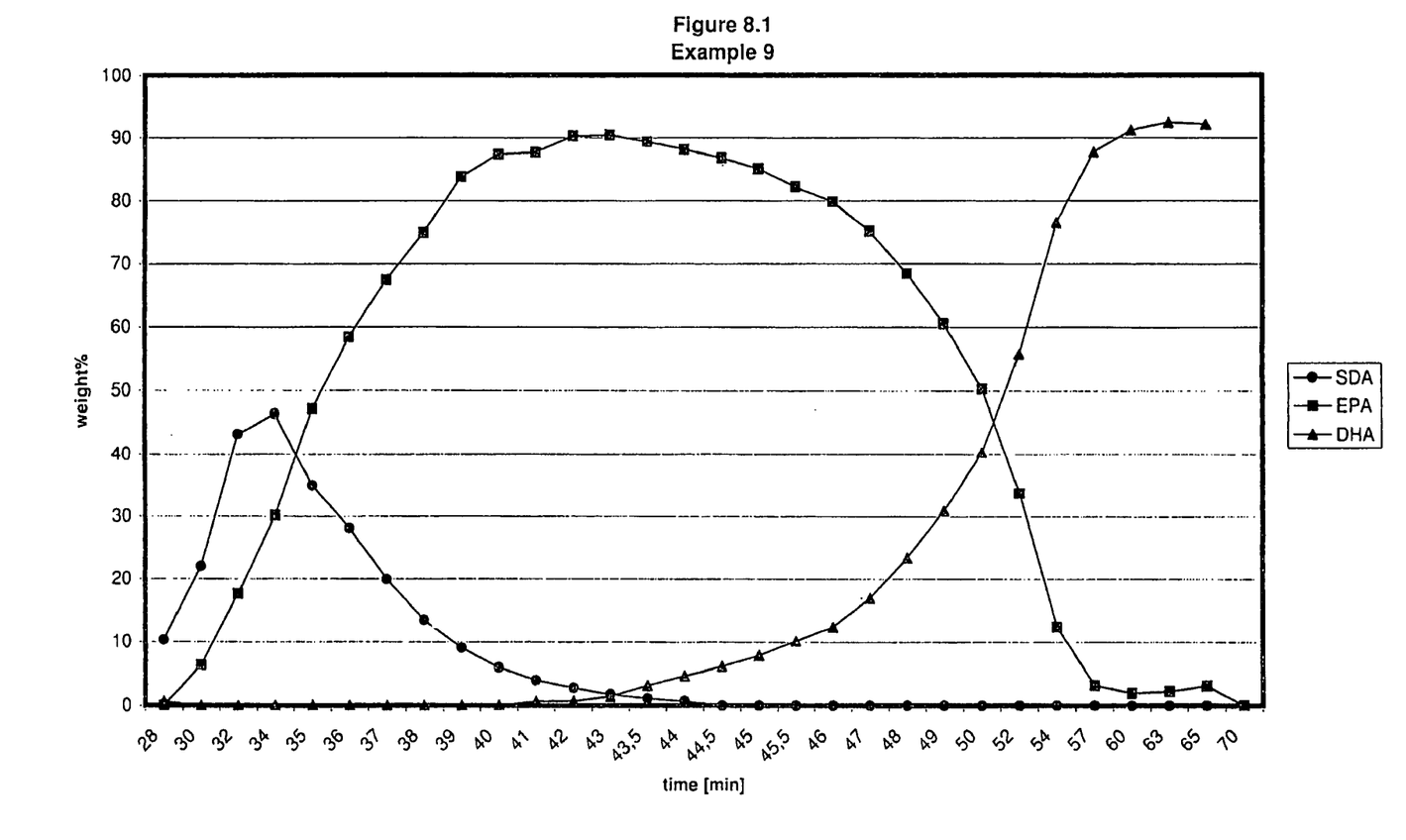

The starting product was applied to the preparative column as above, operated at 103 bar and 46° C. for 40 minutes, whereafter the temperature was decreased within one minute by 26° C. to 20° C. In doing so, the supercritical area of the medium ($CO_2$) is left, and its flui stage (p>per; T<Tcr) is entered. The results can be seen in FIG. 8 which shows that on the said preparative cromatographic column, run with SFC/SFE methods for separating DHA and EPA from each other and, at the same time, from stearidonic acid, it was possible to obtain an EPA fraction with a (rounded off) peak purity of 90% of EPA in 67 min elution time needed to recover both fractions. In this case, there was not only the increase in peak purity reported, but the yield of the EPA>80% fraction was increased to 53%, wheras the yield of the EPA>90% fraction was 17%. This shows a remarkable increase of the quality and yield of the target fraction at equal running time, proving the particularly increased performance of the herein described preferred method. See FIG. 8.1.

Figure 82:
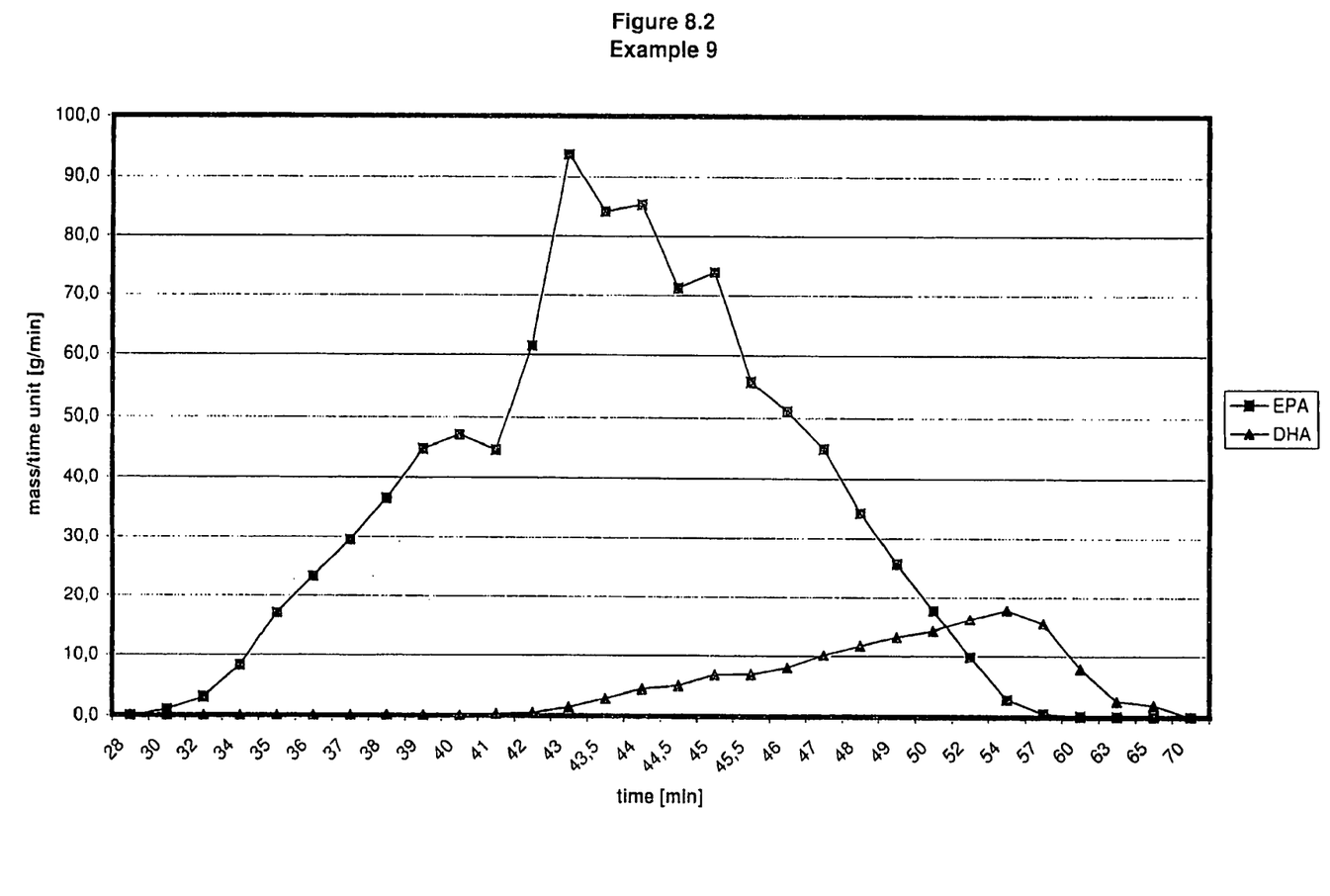

FIG. 8.2 shows the elution profile and discloses that the gradient was applied after having eluted less than 40% of the target substance EPA (c.f. the areas under the respetive peak up to and after 40 minutes).

Example 10

Comparative

The starting product was applied to the preparative column as above, operated at 103 bar and 46° C. The results can be seen in FIG. 9 which shows that on the said preparative cromatographic column, run with SFC/SFE methods for separating DHA and EPA from each other and, at the same time, from stearidonic acid, in order to obtain respective fractions with a (rounded off) peak purity of 85% of EPA, 86 min elution time are needed to recover both fractions. The yield of the EPA>80% fraction was 50%. See FIG. 9.

The conditions applied in examples 6-10 above are thus summarized in table 6.

TABLE 6

Figure 5:
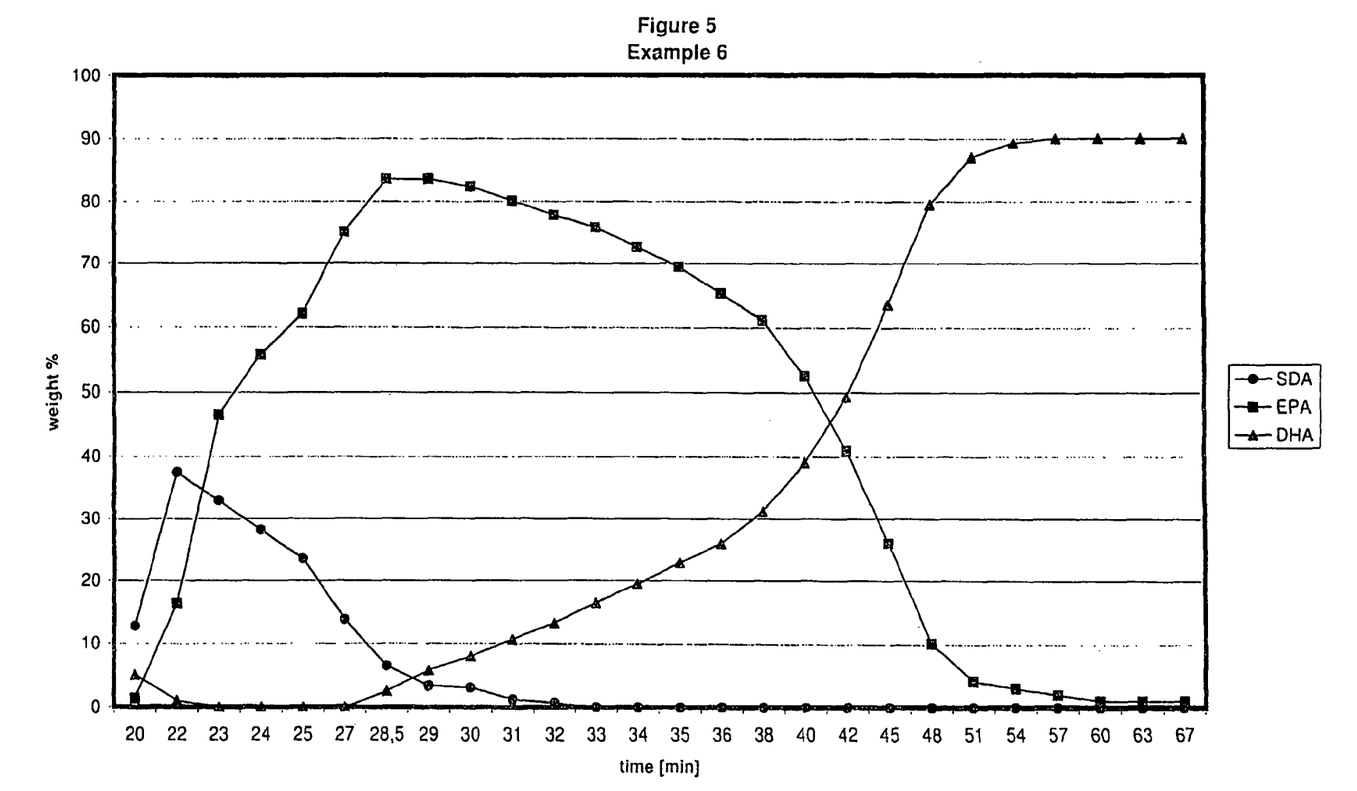
FIG. 5 is a graphic representation of the content ([weight %], y-axis) of EPA, DHA and SDA recorded after a specified elution time ([min], x-axis) at the output of a chromatographic column charged with an aminopropyl phase operated with SFC/SFE using $CO_2$ at 120 bar and 46° C.
Figure 6:
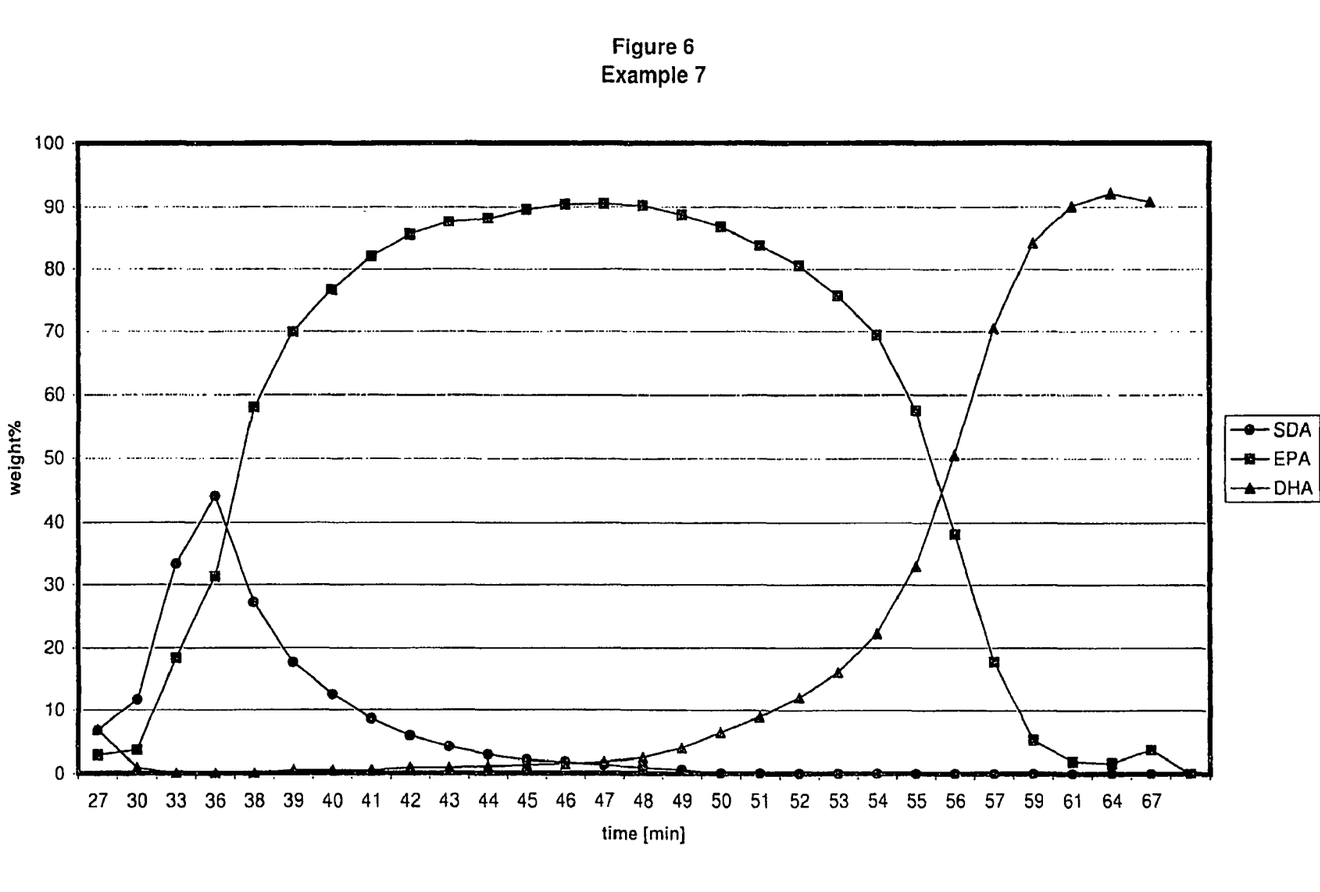
FIG. 6 is a graphic representation of the content ([weight %], y-axis) of EPA, DHA and SDA recorded after a specified elution time ([min], x-axis) at the output of a chromatographic column charged with an aminopropyl phase operated with SFC/SFE using $CO_2$ at 103 bar and 46° C., the pressure having been raised, after 40 minutes elution time, within one minute, by 50 bar to 153 bar.
Figure 7:
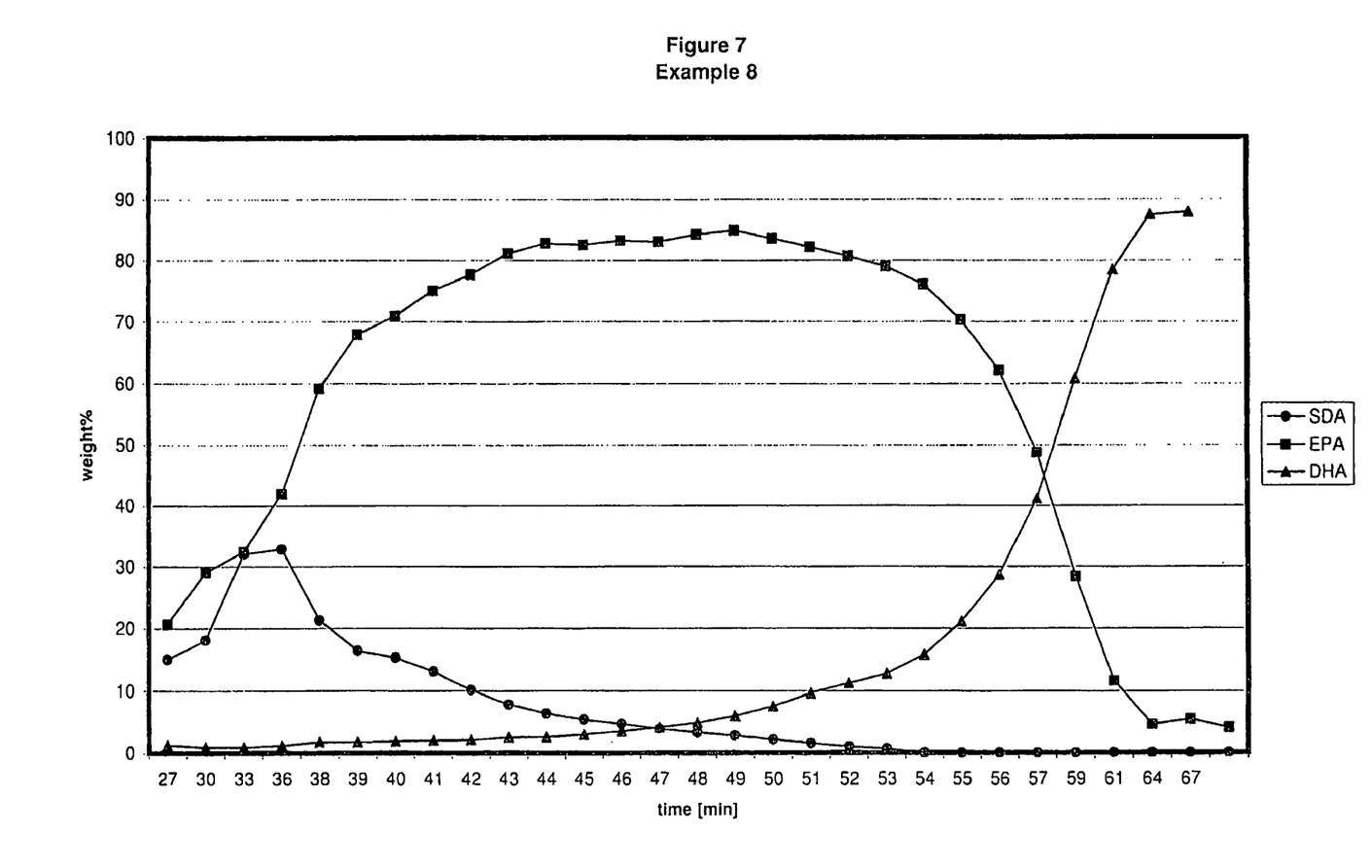
FIG. 7 is a graphic representation of the content ([weight %], y-axis) of EPA, DHA and SDA recorded after a specified elution time ([min], x-axis) at the output of a chromatographic column charged with an aminopropyl phase operated with SFC/SFE using $CO_2$ at 103 bar and 46° C., the temperature having been lowered, after 40 minutes elution time, within one minute, by 6° C. to 40° C.

| | | | | | after 40 min |
|---|---|---|---|---|---|
| | | example 6 (comparative): | | | |
| FIG. 5 | EPA 84% | DHA 87% | 120 bar | 46° C. | — |
| | | Example 7 (invention): | | | |
| FIG. 6 | EPA > 90 | DHA > 90 | 103 bar | 46° C. | +50 bar (→153 bar) |
| | | Example 8 (invention): | | | |
| FIG. 7 | EPA 85% | DHA 90% | 103 bar | 46° C. | −6° C. (→40° C.) |
| | | Example 9 (invention): | | | |
| FIG. 8.1 FIG. 8.2 elution profile | EPA > 90 | DHA > 90 | 103 bar | 46° C. | −26° C. (→20° C.) |
| | | Example 10 (comparative) | | | |
| FIG. 9 | EPA 88% | | 103 bar | 46° C. | — |

The results obtained in examples 6-10 above are summarized in Table 7.

TABLE 7

| | elution time (min.) | Yield "EPA > 80%" | yield "EPA > 90%" |
|---|---|---|---|
| Example 6 (comparative). FIG. 5 (120 bar. 46° C.) | 60 | 26% | 0% |
| Example 7, FIG. 6 (103 bar, switch to 153 bar after 40 min., 46° C.) | 67 | 52% | 14% |
| Example 8, FIG. 7 (103 bar, 46° C., switch to 40° C. after 40 min) | 67 | 47% | 0% |

TABLE 7-continued

Figure 9:
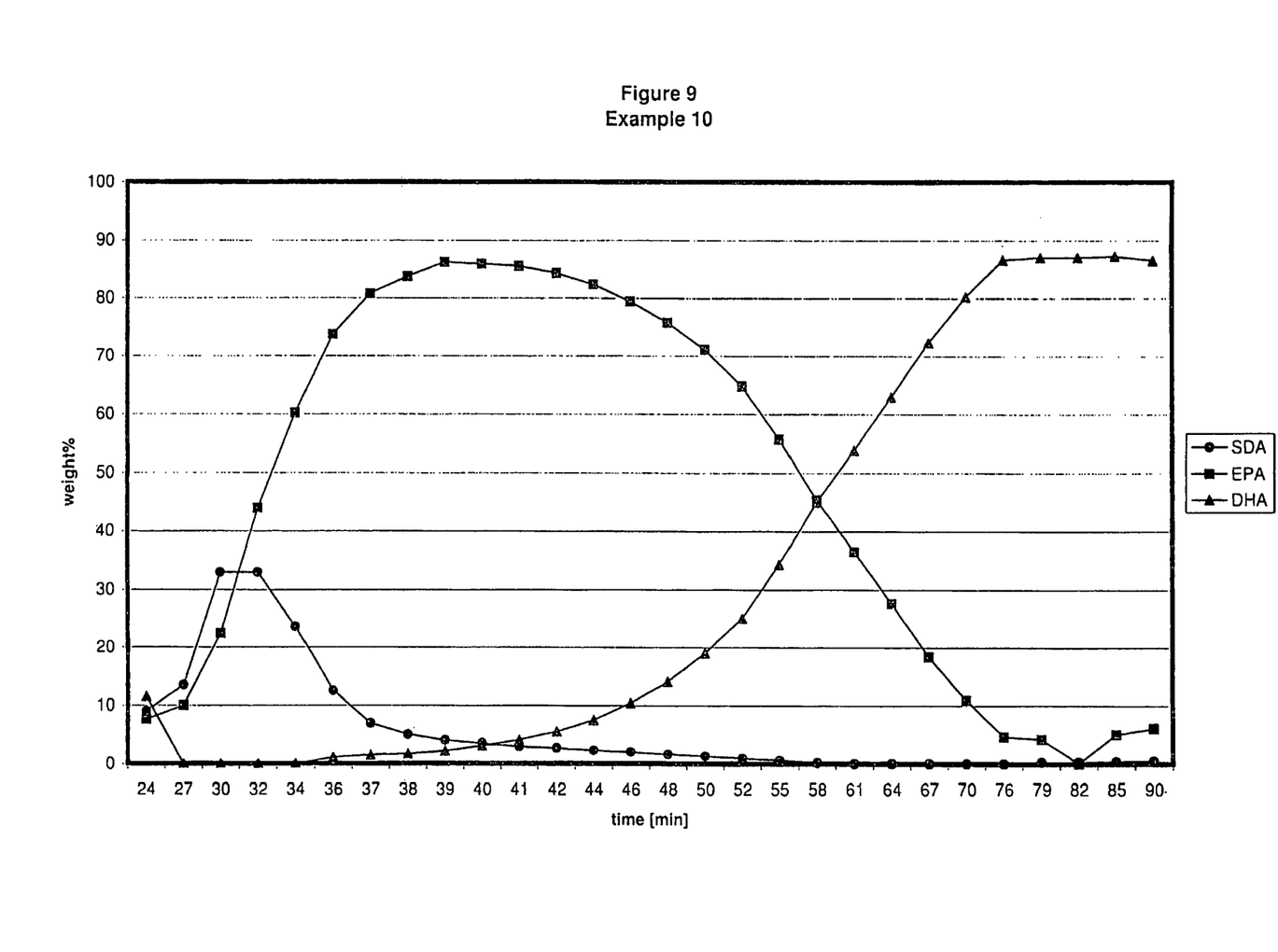
FIG. 9 is is a graphic representation of the content ([weight %], y-axis) of EPA, DHA and SDA recorded after a specified elution time ([min], x-axis) at the output of a chromatographic column charged with an aminopropyl phase operated with SFC/SFE using $CO_2$ at 103 bar and 46° C.

| | elution time (min.) | Yield "EPA > 80%" | yield "EPA > 90%" |
|---|---|---|---|
| Example 9, FIG. 8.1 (103 bar, 46° C., switch to 20° C. after 40 min) | 67 | 53% | 17% |
| Example 10 (comparative), FIG. 9 (103 bar, 46° C.) | 86 | 50% | 0% |

From the above examples 6-10 it thus appears, that compared to an isothermic/isobaric approach (comparative examples 6 and 10), with the adoption of a pressure or a temperature gradient applied during recovery of the EPA fraction, a yield per time increase is obtainable, whithout selectivity loss.

It appears from table 7 that, taking the elution time (example 6, 60 min) as fixed, application of the gradient during recovery of the target substance as herein described, leads not only to an increase in yield, but in some cases surprisingly even to an increase in quality. On the other hand, taken the yield (example 10, about 50%) as fixed, application of the gradient during recovery of the target substance as herein described, leads not only to a decrease in recovery time, but in some cases surprisingly even to an increase in quality.

Examples 1-10 thus show that the inventive method herein described improves the performance a preparative batchwise SFC separation for the recovery of a target substance or a group of target substances from a mixture, without decreasing the selectivity of the ongoing separation.

Glossary:

SFC: Chromatographic method employing a super critical fluid as mobile phase (medium).

SFC/SFE: Chromatographic method employing a super critical fluid as mobile phase (medium), wherein the column is "overcharged", such as to perform, at the same time, supercritical extraction of the substrate, see EP 712 651.

SbFC: Chromatographic method employing a fluid gas (T<Tcr; p>per or T>Tcr; p<per) as mobile phase (medium), see EP 1202 785.

LFC: Chromatographic method employing a liquid gas (T<Tcr; p<per) as mobile phase (medium), see EP 1202 785.

The invention claimed is:

1. Method for improving the performance of a preparative batchwise Super Critical Fluid Chromatographic separation for the recovery of a target fatty acid or derivative thereof, or of a group of target fatty acids or of derivatives thereof from a mixture comprising the step of running the mixture through a chromatographic column charged with a stationary phase chosen from the group consisting of aluminium oxide or aluminium oxides, titanium oxide or titanium oxides, silica gel or silica gels, amino propyl modified silica gels, diol modified silica gels, phenyl modified silica gels and "reversed phase" phases where the stationary phase is chosen from the group consisting of octadecyl carbon chain ($C_{18}$)-bonded silica (RP18), octyl carbon chain ($C_8$)-bonded silica (RP8) and propyl ($C_3$)-bonded silica (RP3), and a mobile phase chosen from the group consisting of ethylene, propane, ammonia, dinitrogen dioxide and CO2, and applying a pressure and/or temperature gradient to the chromatographic column during the elution of the target fatty acid or derivative thereof during the running of the said mixture on the chromatographic column, wherein one or both of the target values set for the pressure and/or temperature gradient applied during elution of the target fatty acid or derivative thereof lie outside a supercritical area of the eluent employed.

2. Method according to claim 1 in which the preparative batchwise Super Critical Chromatographic separation is conducted under conditions allowing, during the Super Critical Chromatographic separation, also for a Super Critical Fluid Extraction.

3. Method according to claim 1, in which the said pressure or temperature gradient or the temperature and pressure gradient is applied in a stepwise manner.

4. Method according to claim 1, in which the said pressure or temperature gradient or the temperature and pressure gradient is applied in a continuous manner.

5. Method according to claim 1, wherein the said pressure or temperature gradient or the temperature and pressure gradient is applied before 85% of the target fatty acid or derivative thereof is eluted.

6. Method according to claim 5, wherein the said pressure or temperature gradient or the temperature and pressure gradient is applied before 50% of the target fatty acid or derivative thereof is eluted.

7. Method according to claim 5, wherein the said pressure or temperature gradient or the temperature and pressure gradient is applied before 40% of the target fatty acid or derivative thereof is eluted.

8. Method according to claim 1, wherein the gradient applied is a temperature gradient, the target value of which is lower than a critical temperature of the eluent employed.

9. Method according to claim 1, in which the eluent employed is $CO_2$.

10. Method according to claim 1 for the separation of fractions enriched with polyunsaturated fatty acids or of their derivatives stemming from natural fish oils.

11. Method according to claim 10 in which the fatty acid derivatives are salts or esters.

12. Method according to claim 11 in which the fatty acid esters are methyl or ethyl esters.

13. Method according to claim 10, in which the polyunsaturated fatty acids are omega-3 acids or their derivatives.

14. Method according to claim 13 for the enrichment of the omega-3 acids EPA or DHA or of their derivatives, wherein the collected EPA- or DHA-rich fractions are characterized by a respective content of at least 80%.

15. Method according to claim 14 for the enrichment of EPA, wherein the collected EPA-rich fraction is characterized by a respective content of at least 80%.

16. Method according to claim 15, wherein the collected EPA-rich fraction is characterized by a respective content of at least 85%.

17. Method according to claim 14 for the enrichment of DHA, wherein the collected DHA-rich fraction is characterized by a respective content of at least 84%.

18. Method according to claim 16, yielding an EPA-enriched fraction of an EPA-content of at least 85% and a DHA-enriched fraction of a DHA content of at least 84%.

* * * * *